United States Patent [19]

Duffett

[11] Patent Number: Plant 6,889

[45] Date of Patent: Jun. 27, 1989

[54] CHRYSANTHEMUM PLANT NAMED PIRANGA

[75] Inventor: William E. Duffett, Salinas, Calif.

[73] Assignee: Yoder Brothers Inc., Barberton, Ohio

[21] Appl. No.: 190,405

[22] Filed: May 5, 1988

[51] Int. Cl.[4] ..... A01H 5/00

[52] U.S. Cl. ..... Plt./82

[58] Field of Search ..... Plt./82

*Primary Examiner*—Robert E. Bagwill

*Attorney, Agent, or Firm*—Foley & Lardner, Schwartz, Jeffery, Schwaab, Mack, Blumenthal and Evans

[57] ABSTRACT

A Chrysanthemum plant named Piranga particularly characterized by its flat capitulum form; decorative capitulum type; red-bronze ray floret color; diameter across face of capitulum of up to 75 mm at maturity; uniform nine week photoperiodic flowering response to short days; peduncle length ranging from 10 to 18 cm on open, terminal sprays; tall plant height when grown as a single stem spray cut mum; and excellent tolerance to low temperatures for bud initiation and flower development.

3 Drawing Sheets

The present invention comprises a new and distinct cultivar of Chrysanthemum, botanically known as *Dendranthema grandiflora,* and referred to by the cultivar name Piranga.

Piranga, identified as 81721003, was originated from a cross made by William E. Duffett in a controlled breeding program in Salinas, Calif. in 1981.

The female parent of Piranga was the cultivar Brass, disclosed in U.S. Plant Pat. No. 5,748. The male parent was an unnamed seedling, identified as 78%73001.

Piranga was discovered and selected as one flowering plant within the progeny of the stated cross by William E. Duffett in August 1981 in a controlled environment in Salinas, Calif.

The first act of asexual reproduction of Piranga was accomplished when vegetative cuttings were taken from the initial selection in November 1981 in a controlled environment in Salinas, Calif., by technicians working under formulations established and supervised by William E. Duffett.

Horticultural examination of controlled flowerings of successive plantings has shown that the unique combination of characteristics as herein disclosed for Piranga are firmly fixed and are retained through successive generations of asexual reproduction.

Piranga has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice. The low temperature tolerance was determined in repeated flowerings in Bogota, Colombia.

The following traits have been repeatedly observed and are determined to be basic characteristics of Piranga, which, in combination, distinguish this Chrysanthemum as a new and distinct cultivar:

1. Flat capitulum form.
2. Decorative capitulum type.
3. Red-bronze ray floret color.
4. Diameter across face of capitulum up to 75 mm at maturity.
5. Uniform nine week photoperiodic flowering response to short days.

6. Peduncle length ranging from 10 to 18 cm on open terminal sprays.
7. Tall plant height, requiring one long day week prior to short days to attain a flowered plant height of 90 to 100 cm for year-round flowerings.
8. Excellent tolerance to low temperatures for bud initiation and flower development.

The accompanying photographic drawings show typical inflorescence and leaf characteristics of Piranga, with the colors being as nearly true as possible with illustrations of this type.

Sheet 1 is a color photograph of Piranga grown as a single stem cut spray mum.

Sheet 2 is a black and white photograph of three views of the inflorescence of Piranga.

Sheet 3 is a black and white photograph showing the upper and under sides of the leaves of Piranga at three stages of development (mature, intermediate and immature).

Of the commercial cultivars known to the inventor, the most similar in comparison to Piranga is Riot, disclosed in U.S. Plant Pat. No. 5,403. Reference is made to Chart A, which compares certain characteristics of Piranga to the same characteristics of Riot.

The ray floret color of Piranga and Riot are both described as red-bronze. Piranga, however, has a more vibrant dark red color compared to the more dull dark red color of Riot. Similar traits are capitulum form and type, flower diameter and flowering response. Piranga has longer peduncles, a taller plant height and a superior tolerance to low temperatures when compared to Riot.

In the following description, color references are made to The Royal Horticultural Society Colour Chart. The exact ray floret color of Piranga is not represented in The Royal Horticultural Society Colour Chart, and the color values given are those closest to the actual color of Piranga. The color values were determined on plant material grown in Salinas, Calif. on Oct. 17, 1987.

Classification:

*Botanical.*—*Dendranthema grandiflora,* cv Piranga.

*Commercial.*—Decorative cut spray mum.

INFLORESCENCE

A. Capitulum:

*Form.*—Flat.

*Type.*—Decorative.

*Diameter across face.*—Up to 75 mm at maturity.

B. Corolla of ray florets:

*Color (general tonality from a distance of three meters).*—Red-bronze.

*Color (upper surface).*—34A to 34B.

*Color (under surface).*9B, overlaid with 34B.

*Shape.*—Flat, oblong.

C. Corolla of disc florets: Flowers are fully double. No disc florets are present.

D. Reproductive organs:

*Androecium.*—Not present.

*Gynoecium.*—Present on ray florets.

PLANT

A. General appearance:

*Height.*—Tall; 90 to 100 cm as a single stem cut mum with one long day week prior to short days.

B. Foliage:

*Color (upper surface).*—147A.

*Color (under surface).*—147B.

*Shape.*—Lobed and slightly serrated.

CHART A

COMPARISON OF PIRANGA AND RIOT

| | Piranga | Riot |
|---|---|---|
| Ray floret color | Red bronze | Red bronze |
| Capitulum form and type | Flat Decorative | Flat Decorative |
| Spray formation | Terminal 10 to 18 cm | Terminal 10 to 12 cm |
| Diameter across face of capitulum | Up to 75 mm | Up to 75 mm |
| Plant height | Tall | Medium |
| Flowering response period | 9 weeks | 9 weeks |
| Low temperature tolerance | Excellent | Marginal |

COMPARISONS MADE OF PLANTS GROWN AS SINGLE STEM SPRAY CUT MUMS IN SALINAS, CALIFORNIA

I claim:

1. A new and distinct Chrysanthemum plant named Piranga, as described and illustrated, and parts thereof.

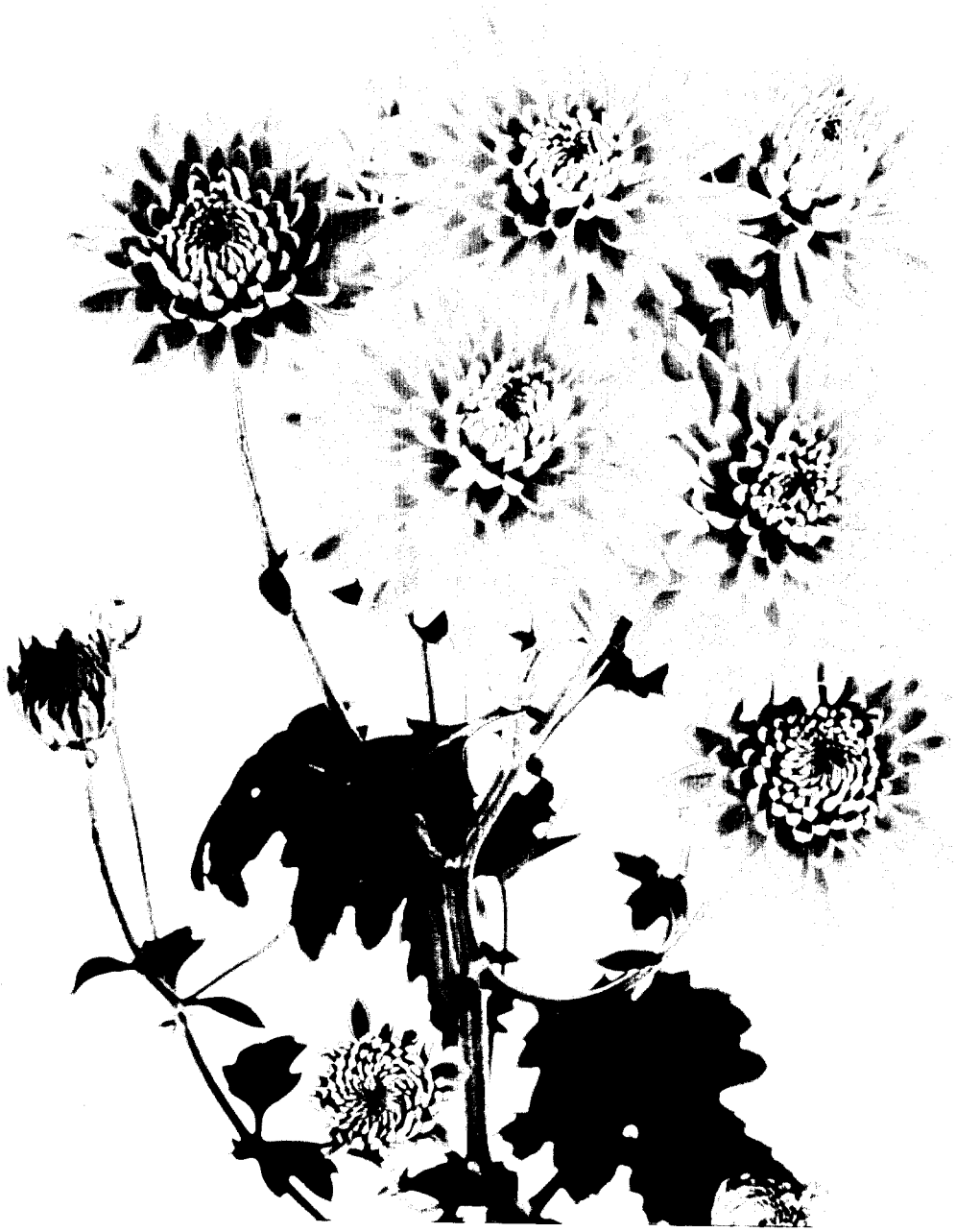

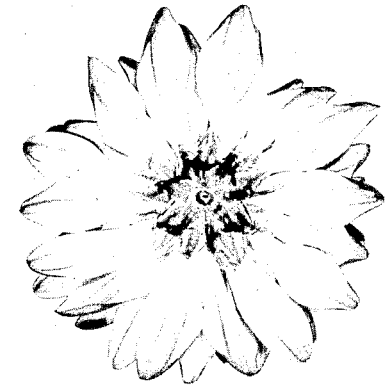
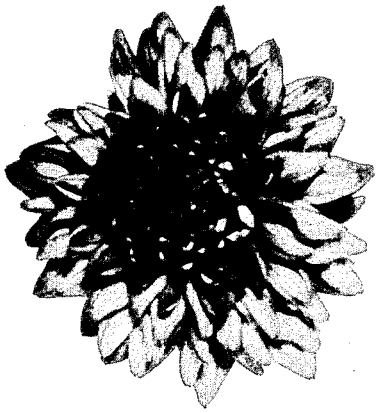
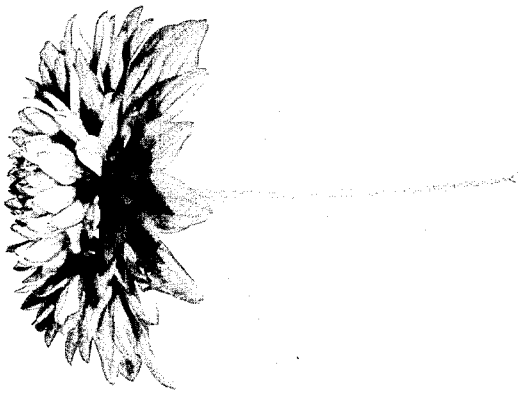

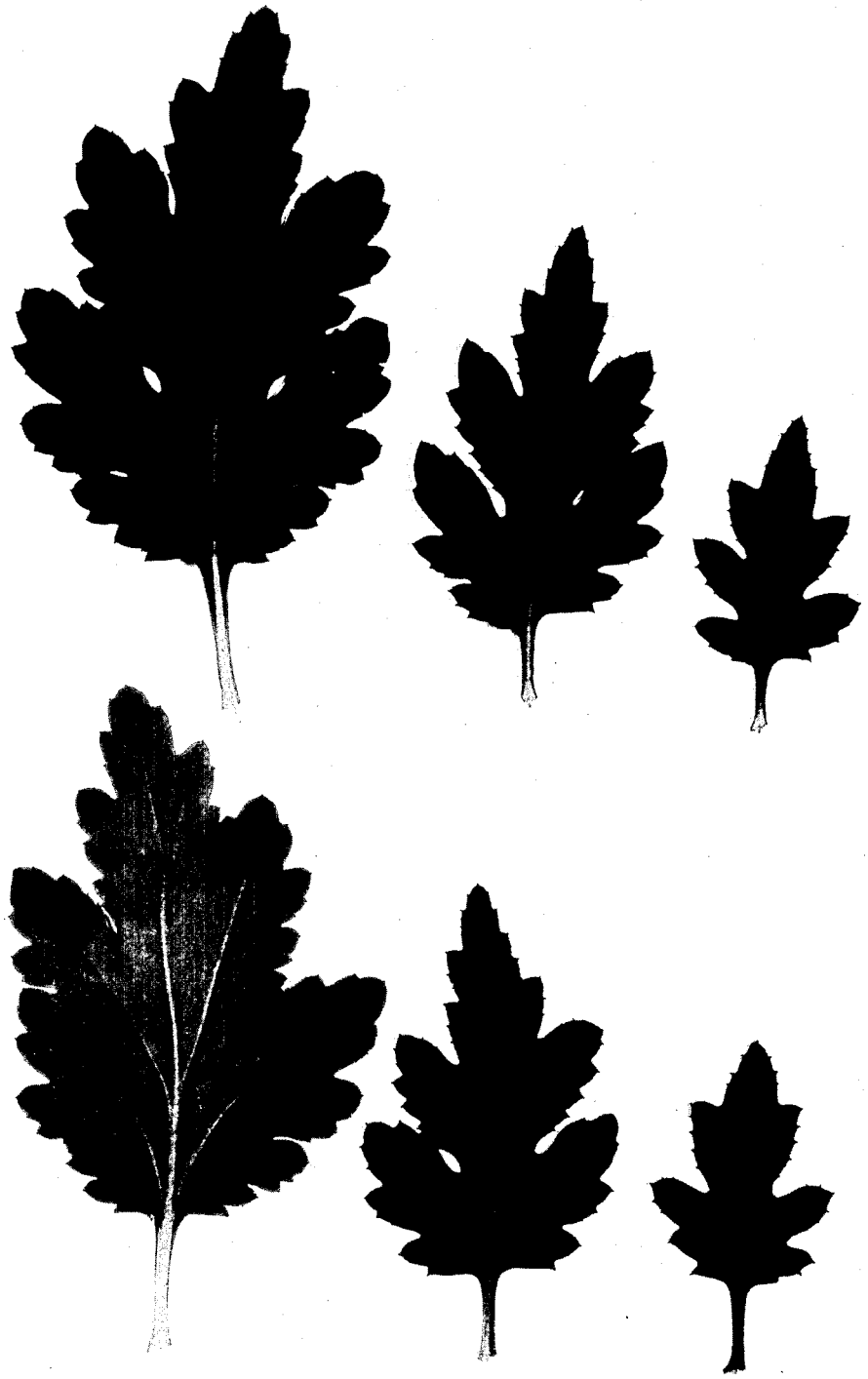

* * * * *